US012635878B2

(12) United States Patent
Roodaki et al.

(10) Patent No.: US 12,635,878 B2
(45) Date of Patent: May 26, 2026

(54) MICROSCOPE

(71) Applicant: Carl Zeiss Meditec AG, Jena (DE)

(72) Inventors: Hessam Roodaki, Munich (DE);
Abouzar Eslami, Munich (DE)

(73) Assignee: Carl Zeiss Meditec AG, Jena (DE)

( * ) Notice: Subject to any disclaimer, the term of this
patent is extended or adjusted under 35
U.S.C. 154(b) by 206 days.

(21) Appl. No.: 17/691,995

(22) Filed: Mar. 10, 2022

(65) Prior Publication Data

US 2022/0287561 A1 Sep. 15, 2022

(30) Foreign Application Priority Data

Mar. 11, 2021 (DE) ..................... 10 2021 202 384.3

(51) Int. Cl.
*A61B 3/13* (2006.01)
*A61B 3/10* (2006.01)
*G06T 7/73* (2017.01)

(52) U.S. Cl.
CPC ............... *A61B 3/13* (2013.01); *A61B 3/102*
(2013.01); *G06T 7/73* (2017.01); *A61B*
*2560/0223* (2013.01); *G06T 2207/10101*
(2013.01); *G06T 2207/30204* (2013.01)

(58) Field of Classification Search
CPC ...... A61B 2034/2068; A61B 2034/207; A61B
2560/0223; A61B 2090/062; A61B
2090/3735; A61B 2090/3995; G06T 7/73;
G06T 2207/30204; G06T 2207/30208
See application file for complete search history.

(56) References Cited

U.S. PATENT DOCUMENTS

| | | | |
|---|---|---|---|
| 2004/0054489 A1* | 3/2004 | Moctezuma De La Barrera ........ G16Z 99/00 702/105 |
| 2004/0167393 A1* | 8/2004 | Solar ...................... A61B 90/39 600/414 |
| 2014/0024949 A1 | 1/2014 | Wei et al. | |
| 2014/0221822 A1 | 8/2014 | Ehlers et al. | |
| 2015/0173644 A1 | 6/2015 | Ren et al. | |
| 2015/0342460 A1 | 12/2015 | Izatt et al. | |

(Continued)

FOREIGN PATENT DOCUMENTS

| | | |
|---|---|---|
| DE | 102011015149 A1 | 9/2012 |
| DE | 102020102011 A1 | 7/2021 |

(Continued)

OTHER PUBLICATIONS

Office Action issued in German Patent Application No. DE 10 2021
202 384.3, dated Sep. 22, 2021 (from which this application claims
priority) and English language translation thereof.

(Continued)

*Primary Examiner* — Uzma Alam

(74) *Attorney, Agent, or Firm* — Ewers IP Law PLLC;
Falk Ewers

(57) ABSTRACT

A microscope is provided which includes an optical module,
an OCT module, and a control device. The optical module
is configured to generate optical image representations. The
OCT module is configured to generate tomographic record-
ings. The control device is configured to determine the
relative spatial position of a marking element, in each case
from an optical image representation of the marking element
and from a tomographic recording of the same marking
element.

17 Claims, 3 Drawing Sheets

(56)         References Cited

U.S. PATENT DOCUMENTS

| | | |
|---|---|---|
| 2016/0324593 A1 | 11/2016 | El-Haddad et al. |
| 2018/0168737 A1 | 6/2018 | Ren et al. |
| 2020/0129056 A1* | 4/2020 | Soma ..................... A61B 3/102 |
| 2021/0228284 A1 | 7/2021 | Voigt et al. |
| 2022/0125302 A1* | 4/2022 | Buckland ............... A61B 3/102 |
| 2025/0085104 A1* | 3/2025 | Binder ................. G01B 11/026 |

FOREIGN PATENT DOCUMENTS

| | | |
|---|---|---|
| EP | 3603484 A1 | 2/2020 |
| WO | 2013059719 A2 | 4/2013 |

OTHER PUBLICATIONS

Summons to Hearing of the German Patent and Trademark Office dated Jan. 24, 2022 (Priority Application No. DE 10 2021 202 384.3) and English-language translation thereof.

* cited by examiner

MICROSCOPE

CROSS REFERENCE TO RELATED APPLICATIONS

This application claims priority to German patent application DE 10 2021 202 384.3, filed Mar. 11, 2021, the entire content of which is incorporated herein by reference.

TECHNICAL FIELD

The disclosure relates to a microscope, to a system including a microscope and a marking element, and to a medical instrument. Furthermore, the disclosure relates to a method for calibrating a microscope.

BACKGROUND

In order to obtain particularly reliable examination results and to facilitate particularly precise treatments, for example in ophthalmology or in brain surgery, microscopes used to this end sometimes have an optical coherence tomography (OCT) module for generating a tomographic recording within the examination region, in addition to the components for generating a magnified image representation of an examination region. The magnified image representation is also referred to as microscope image below. The tomographic recording is also referred to as OCT image below.

OCT represents an abbreviation for optical coherence tomography. In the case of optical coherence tomography, light in the infrared range is radiated onto body tissue and, as a rule, said infrared light penetrates a few millimeters into the body tissue. The light scattered back from different depths of the body tissue is detected and a tomographic recording is generated therefrom.

Both the microscope image and the OCT image can be displayed on a visual display unit and provide the treating physician with information about the examination region. Moreover, the microscope image and the OCT image may also contain information in respect of a medical instrument used during the examination or treatment.

US 2014/0221822 A1 describes the practice of determining the depth coordinate of a medical instrument by OCT and, in particular, of determining a position of the medical instrument relative to a target. EP 3603484A1 describes an information processing device which collects information about a marking element represented in a tomographic recording. A position or alignment of a medical instrument containing the marking element and being used during a medical treatment is determined from the information.

To facilitate a defined mapping between the microscope image and the OCT image, a calibration between the components for generating the image representation and the OCT module may be performed when the microscope is produced. However, different influences may lead to errors post calibration, which may add up over time to form significant discrepancies between the microscope image and the OCT image.

In this context, unconsidered external factors such as the effect of the surroundings during transport, changes in the operating temperature and long-term effects of the use of the microscope, for example, may have an impact. Moreover, the calibration in ophthalmology applications is generally performed on the basis of a standard model of the eye, and so individual optical deviations of the eye of the patient remain unconsidered as a rule.

A further difficulty arises due to the fact that externally arranged OCT modules are used ever more frequently with the microscopes, these OCT modules not being rigidly connected to the microscope but being more susceptible to external mechanical influences in comparison with integrated OCT modules, and so misalignments may arise more frequently.

SUMMARY

It is an object of the disclosure to provide a permanent reliable mapping in a microscope between a microscope image and an OCT image or data connected therewith.

The object is achieved by a microscope, a medical instrument, a system, a method for calibrating a microscope, and a non-transitory computer-readable storage medium as described herein.

The microscope according to an aspect of the disclosure includes an optical module, an OCT module and a control device in communication with the optical module and the OCT module. The optical module is configured to generate optical image representations. The OCT module is configured to generate tomographic recordings. The control device is configured to determine the relative spatial position of a marking element, in each case from an optical image representation of the marking element and from a tomographic recording of the same marking element.

The disclosure has the advantage of facilitating a permanent reliable mapping between a microscope image and an OCT image or data connected therewith. This mapping is established by way of a marking element, the relative spatial position of which the microscope determines firstly from an optical image representation, that is to say a microscope image, and secondly from a tomographic recording, that is to say an OCT image.

The control device can be configured to perform a calibration between the optical module and the OCT module on the basis of the optical image representation and the tomographic recording of the marking element. As a result, a precise mapping between microscope images and OCT images or the data connected therewith is possible, even after an extended period of use of the microscope.

The disclosure also relates to a medical instrument including a marking element having a depression and/or an elevation. The depression and/or the elevation is embodied such that the relative spatial position of the marking element is determinable from an optical image representation of the depression and/or the elevation and the relative position of the marking element is also determinable from a tomographic recording of the depression and/or elevation.

The medical instrument according to an aspect of the disclosure has the advantage of facilitating a calibration of a microscope with very little outlay and virtually at any desired time, in particular even during the use of the medical instrument within the scope of a medical treatment. As a result, a possible misalignment between the optical module of the microscope and the OCT module can be determined quickly and reliably.

The disclosure also relates to a system including a microscope and a marking element. The microscope has an optical module, with which an optical image representation of the marking element is generable. Furthermore, the microscope has an OCT module, with which a tomographic recording of the marking element is generable. The marking element is designed such that the relative spatial position of the marking element is determinable both from the optical image representation of the marking element and from the tomographic recording of the marking element. Furthermore, the system has a control device which is configured to determine the relative spatial position of the marking element both from the optical image representation of the marking element and from the tomographic recording of the marking element.

Great precision of the mapping of images and/or data generated firstly by the optical module and secondly by the OCT module of the microscope can be obtained using such a system. Moreover, the system has great long-term stability.

The control device can be designed as a component of the microscope. This facilitates a compact structure.

In particular, a mode of operation can be implemented in the microscope, within the scope of which the relative spatial position of the marking element is determined both from the optical image representation of the marking element and from the tomographic recording of the marking element. This means that the complete functionality for determining the relative position of the marking element can be located intrinsically in the microscope.

The marking element can have a locally varying characteristic that is detectable both by using the optical module and by using the OCT module. Such a characteristic facilitates determination of the relative spatial position of the marking element with comparatively little outlay.

The characteristic may have a feature that is identifiable both in the optical image representation of the marking element and in the tomographic recording of the marking element. This facilitates a particularly simple and compact form of the marking element. It is likewise also possible for the characteristic to have a first feature that is identifiable in the optical image representation of the marking element and a second feature that is identifiable in the tomographic recording of the marking element. This implementation variant allows the respective feature to be optimally calibrated for the respective detection method.

The locally varying characteristic of the marking element may have a strictly monotonic form. This is advantageous in that there is a unique mapping between each value determined for the characteristic and the associated location of the marking element, and ambiguities during the determination of the relative spatial position can be avoided.

The characteristic may vary from one end of the marking element to an opposite end of the marking element. In particular, the characteristic may vary continuously. Both contribute to obtaining high accuracy.

The marking element may have an outer shape which is configured such that the relative spatial position of the marking element is determinable from the tomographic recording of the outer shape of the marking element. Such an embodiment is comparatively easy to produce and moreover reliably detectable using the OCT module.

The outer shape of the marking element may have at least one depression and/or at least one elevation. Such a structure has advantages during the manufacturing thereof and is very robust. The depression and/or the elevation may have a varying width. In particular, the width of the depression and/or of the elevation may vary strictly monotonically from one end to an opposite end of the depression and/or elevation. As a result, it is possible to avoid ambiguities when determining the relative spatial position of the marking element from the tomographic recording of the marking element.

Further, the width of the depression and the width of the elevation can vary in the same sense. The depression may have a constant maximum depth from one end of the depression to the opposite end. The elevation may have a constant maximum height from one end of the elevation to the opposite end. The depression and/or the elevation may have an elongate form. The lateral distance between the locations on the marking element where the maximum depth is present and the locations on the marking element where the maximum height is present may be constant. A marking element formed thus represents a good compromise between simple producibility on the one hand and precision and reliability of the results obtainable therewith on the other hand.

The marking element may have regions with different reflectivity. In particular, the depression may have a different reflectivity to the elevation. This represents a simple-to-realize option for a reliable detection of the individual regions using the optical module.

The marking element can be in the form of a segment of a hollow cylinder. Such a form is particularly well suited to the arrangement of the marking element on a medical instrument which, as a rule, has a cylindrical shaft.

In particular, the marking element may be arranged on a medical instrument. Since a medical instrument is used in any case for many medical treatments in which the microscope is used, there thus is hardly any additional outlay for the provision of the marking element in a region that is detectable both by the optical module and by the OCT module.

By way of example, the marking element may be engraved into the medical instrument. In particular, the marking may be formed with laser marking. Likewise, the marking element may be formed as a separate component and fastened to the medical element. The marking element may be integrally bonded to the medical instrument. In particular, the marking element may be fastened to the medical instrument with an adhesive connection. Likewise, the marking element may be fastened to the medical instrument in interlocking fashion or in frictionally connected fashion. Which is the optimal implementation variant depends in each case on, for example, the field of application, the form of the medical instrument, the required accuracy, the admissible outlay, etc.

The disclosure also relates to a method for calibrating a microscope which has an optical module and an OCT module. In the method according to the disclosure, an optical image representation of a marking element is generated with the aid of the optical module and a tomographic recording of the marking element is generated with the aid of the OCT module. A first determination of the relative spatial position of the marking element, which leads to a first result, is carried out on the basis of the optical image representation of the marking element. A second determination of the relative spatial position of the marking element, which leads to a second result, is carried out on the basis of the tomographic recording of the marking element.

The method according to the disclosure represents a very efficient option for calibrating a microscope that has an optical module and an OCT module. No complicated calibration equipment is required, and the use of the microscope is not restricted or only slightly restricted.

Within the scope of the method according to the disclosure, a deviation can be determined between the first result and the second result.

A test to determine whether an inadmissibly significant misalignment is present between the optical module and the OCT module can be carried out on the basis of the determined deviation. By way of example, the determined deviation can be compared with a specified maximum value for the deviation. In this case, an inadmissibly significant misalignment can be deduced if the determined deviation exceeds the specified maximum value for the deviation. The misalignment can be reduced by a readjustment in the case of an inadmissibly significant misalignment. In particular, the optical module and/or the OCT module can be read-justed. It is likewise also possible to determine correction values from the misalignment, these correction values being taken into account within the scope of the representation or the evaluation of the optical image representation and/or the tomographic recording. No mechanical intervention is required in this procedure.

The calibration can be prompted in each case when a specified condition is present. This facilitates a calibration strategy that is optimally tailored to the use of the micro-scope.

By way of example, the specified condition may be the activation of the microscope, in particular the respective activation prior to a medical treatment or a series of medical treatments. The advantage thereof is that the treatment or the series of treatments is started with a newly calibrated microscope.

Likewise, the specified condition can be that a specified time has elapsed since the last calibration. As a result, a perpetual calibration at predetermined time intervals is achieved and a good calibration is permanently ensured. The specified condition may also consist in the calibration being prompted manually. This facilitates a needs-based calibra-tion.

There is the option within the scope of the method according to the disclosure of the calibration being per-formed during a medical treatment. The advantage thereof is that the calibration is performed under the same conditions under which the medical treatment is also carried out, and hence this calibration supplies particularly precise results. In particular, this also provides the option of an application-specific calibration. By way of example, the calibration may be performed specifically for each patient treated with the aid of the microscope. When using the method according to the disclosure in ophthalmology, there is the advantage that individual optical conditions, for example the refractive power of the lens of the treated eye, can be taken into account during the calibration so that a very high accuracy can be obtained.

The disclosure also relates to a non-transitory computer-readable storage medium with a computer program includ-ing a program code that when executed by a processor causes the processor to carry out the method according to the disclosure and/or the implementation of said method.

Finally, the disclosure relates to a method for the medical treatment and/or examination using a microscope, wherein a calibration is performed between an optical module and an OCT module of the microscope during the medical treat-ment and/or examination. The calibration may be performed in the manner described above.

BRIEF DESCRIPTION OF THE DRAWINGS

The disclosure will now be described with reference to the drawings wherein.

DESCRIPTION OF EXEMPLARY
EMBODIMENTS

Figure 1:
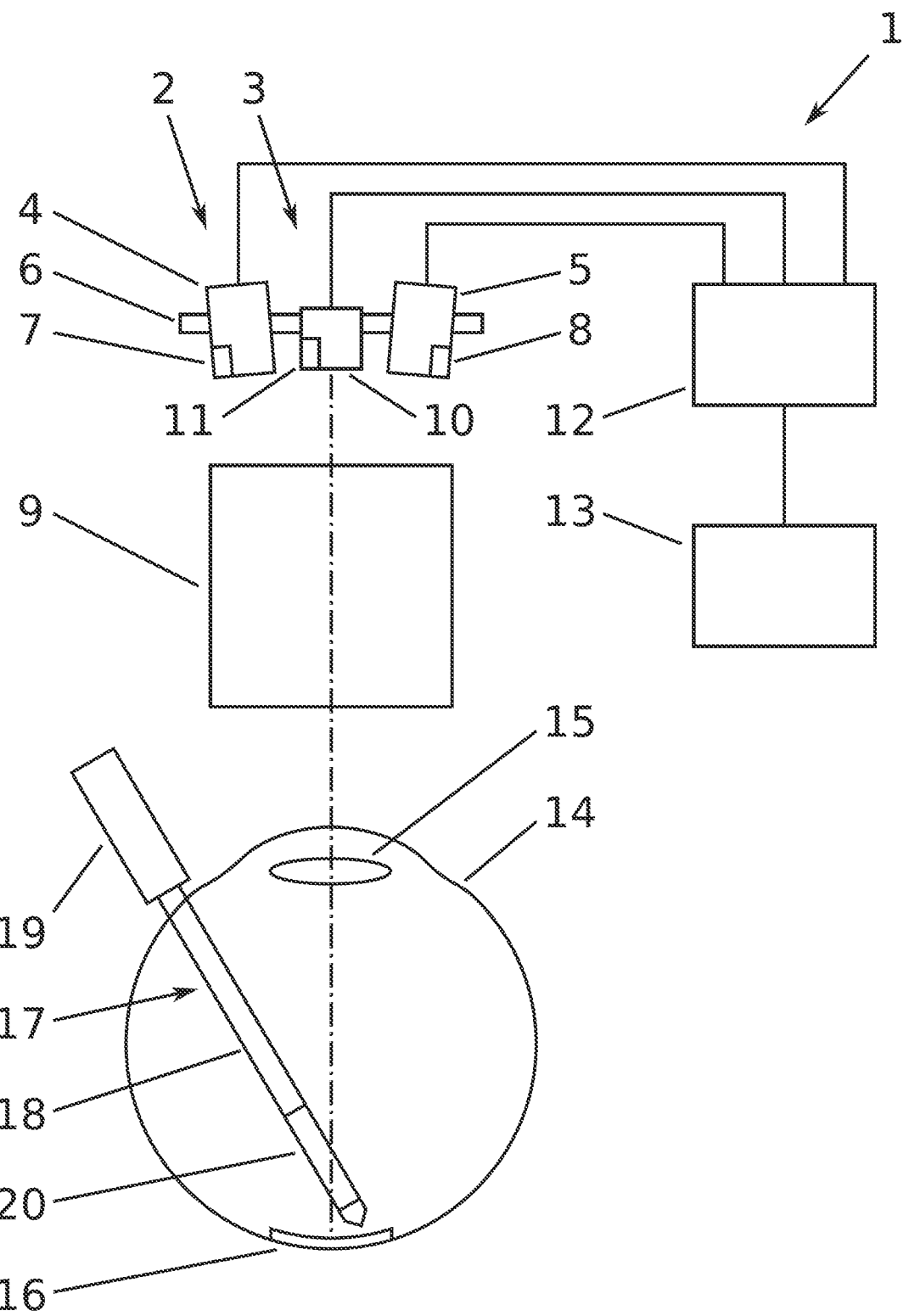
FIG. 1 shows a schematic plan view of a microscope in a typical use situation according to an exemplary embodiment of the disclosure.

FIG. 1 shows a schematic plan view of a microscope 1 in a typical use situation according to an exemplary embodi-ment of the disclosure. The representation is very abstract and only illustrates components of significance to the under-standing of the disclosure.

The microscope 1 has an optical module 2 and an OCT module 3. In this case, OCT represents an abbreviation for optical coherence tomography.

In the case of optical coherence tomography, light in the infrared range is radiated onto body tissue and, as a rule, said infrared light penetrates a few millimeters into the body tissue. The light has a comparatively short coherence length of typically a few micrometers. The light is scattered along its path through the body tissue in a manner depending on the locally varying characteristics of the body tissue, with a small proportion of the light being reflected back to the OCT equipment in each case and being overlaid there with reference light. The interference pattern generated by the superposition is detected and evaluated. In this case, depth information for the respectively detected light can be deter-mined by virtue of the reference light being split from the radiated-in light, for example with a semi-transmissive mir-ror and being subjected to a varying degree of retardation prior to the superposition. Since interference as a result of a coherent superposition only occurs within the coherence length of the light, the respectively associated depth, from which the light was reflected back, can be determined very precisely. As a rule, the obtainable accuracy is of the order of half the coherence length of the utilized light. By way of example, the result of the evaluation can be represented as an image that represents a section through the examined body tissue. To obtain a two-dimensional image, the light can be scanned over the body tissue such that the body tissue is irradiated within a line-shaped region of incidence. This is also referred to as a B-scan below. With a plurality of B-scans with adjacent regions of incidence, it is also pos-sible to combine the individual sections to form a three-dimensional representation.

The optical module 2 has a first microscope camera 4 and a second microscope camera 5, which are fastened to a frame 6 at a distance from one another such that they include a small angle. Expressed differently, the orientation of the first microscope camera 4 and of the second microscope camera 5 in relation to one another deviates only slightly from a parallel alignment. Furthermore, the optical module 2 has a first illumination device 7 and a second illumination device 8. The first illumination device 7 is attached to the first microscope camera 4. The second illumination device 8 is attached to the second microscope camera 5. The illumi-nation devices 7, 8 may also be integrated in the microscope cameras 4, 5 or be arranged at other locations. Moreover, the optical module 2 includes an optical unit 9.

The OCT module 3 has an OCT detector 10 and an OCT illumination device 11. The OCT detector 10 is fastened to the frame 6 between the first microscope camera 4 and the second microscope camera 5 and oriented such that the OCT detector 10 bisects the angle between the first microscope camera 4 and the second microscope camera 5. The OCT illumination device 11 is attached to the OCT detector 10. Alternatively, the OCT illumination device 11 may also be integrated in the OCT detector 10 or be arranged at any other location.

The first microscope camera 4, the second microscope camera 5 and the OCT detector 10 are each electrically connected to a control device 12, which for example may be in the form of a computer system and may have a processor which executes a computer program. In turn, the control device 12 is connected to a visual display unit 13.

Furthermore, FIG. 1 illustrates an eye 14, which is examined and/or treated by the microscope 1 and which has a lens 15. The optical module 2 and the OCT module 3 are arranged relative to the eye 14 such that this facilitates, through the lens 15 of the eye 14, an observation of the interior of the eye 14 and, in particular, of a treatment region 16, within which a medical examination and/or treatment is carried out. In this case, the optical unit 9 is arranged between the eye 14 and the microscope cameras 4, 5. The optical unit 9 may be in the form of a magnification optical unit for the microscope cameras 4, 5 and, for example, may generate a magnified image of a desired region of the eye 14. To this end, the optical unit 9 can be configured such that a separate partial optical unit is provided for each microscope camera 4, 5. However, it is also possible to configure the optical unit 9 such that a common optical unit is provided for both microscope cameras 4, 5. Likewise, it is possible to combine two partial optical units and a common optical unit. In all variants it is possible to also use the optical unit 9 for the measurements using the OCT detector 10, or to equip the OCT detector 10 with a separate OCT optical unit.

A medical instrument 17 has been introduced into the eye 14. The medical instrument 17 has a cylindrical shaft 18 in the depicted exemplary embodiment. A handle 19 is attached to the region of one end of the shaft 18 which is arranged outside of the eye 14. In the vicinity of its other end of the shaft 18, the medical instrument 17 has a marking element 20. The end of the shaft 18 with the marking element 20 arranged in the vicinity thereof is configured in accordance with the functionality apportioned to the medical instrument 17. The end of the shaft 18 may have a rigid form and, for example, have a blade, a hook, etc. It is likewise also possible for the end of the shaft 18 to have a movable design, for example as forceps, scissors, etc. Accordingly, the medical instrument may be configured as, for example, an endoillumination probe, vitreoretinal forceps, vitreoretinal scissors, etc.

To perform a medical examination or a medical intervention on a patient with the microscope 1, the microscope 1 and the patient are positioned relative to one another so that the eye 14 of the patient to be treated is arranged relative to the microscope 1 as shown in FIG. 1. Then, the eye 14 is illuminated with the first illumination device 7, the second illumination device 8 and the OCT illumination device 11. The treatment region 16 of the eye 14 or a portion thereof is imaged with the optical unit 9 and magnified image representations of the treatment region 16, which are also referred to as microscope images below, are generated together with the microscope cameras 4, 5. As a rule, the medical instrument 17 which is arranged in the vicinity of the treatment region 16 and, in particular, the marking element 20 arranged on said medical instrument are also imaged in this case.

Moreover, a B-scan is generated with the OCT detector 10 along a line within the treatment region 16. Likewise, it is also possible to generate a plurality of B-scans within the treatment region 16. In the following text, the B-scans are also referred to as OCT images.

The microscope image data are transmitted from the microscope cameras 4, 5 to the control device 12. Furthermore, the OCT image data are transmitted from the OCT detector 10 to the control device 12. From the microscope image data and the OCT image data, the control device 12 generates data for a combined representation and transmits these data to the visual display unit 13. The visual display unit 13 displays a combined representation, which contains both information from the microscope images and information from the OCT images.

Both microscope images and/or information derived therefrom, and also OCT images and/or information derived therefrom, that is to say, for example, B-scans or three-dimensional OCT images, can be presented on the visual display unit 13. In particular, the OCT images can be overlaid on the microscope images or related thereto in any other way, and/or the respectively associated information may be presented.

By way of example, the visual display unit 13 displays a combined image containing both the microscope image and the OCT image. In this case, the microscope image and the OCT image are processed in the presentation of the visual display unit 13 in such a way that, despite the different nature of the data from which they are produced, a common presentation which represents an added value to the physician is possible. The different nature of the data is based on the fact that the microscope image represents a plan view of the treatment region 16 and the medical instrument 17 positioned there, while the OCT image represents a section through the tissue and the medical instrument 17 within the treatment region 16.

The combined representation allows the physician, with one glance, to equally register for example the surface of the tissue in the treatment region 16 and a section through the tissue within the treatment region 16.

To obtain optimal use, it is in each case advantageous or even mandatory for the optical module 2 and the OCT module 3 to be calibrated with respect to one another. What this can achieve, for example, is that the OCT image is recorded for a location in a region to be examined which is identifiable in the microscope image.

By way of example, an initial calibration can be performed by way of an alignment of the microscope cameras 4, 5 and the OCT detector 10 when the microscope 1 is produced. Depending on the embodiment, the optical unit 9 may also be included in the alignment. However, this alignment may increasingly be lost over time as a result of external influences such as impacts, temperature changes and long-term drifts. Moreover, the individual optical characteristics of the eyes 14 of the respective patient cannot be taken into account during this alignment. It is for this reason that the first calibration is followed by further calibrations within the scope of the disclosure. By way of example, these calibrations can be performed at the start of a respective treatment of a patient. It is likewise also possible to perform the calibrations at predetermined time intervals or when any specified conditions occur or else following the prompt of the treating physician. A continuous or quasi-continuous calibration during the treatment of the patient is also possible.

The calibration is performed with the aid of the marking element 20. In this case, the calibration is based on the principle that a relative spatial position of the marking element 20 determined with the aid of the optical module 2 and a relative spatial position of the marking element 20 determined with the aid of the OCT module 3 correspond exactly in the case of a perfect calibration of the microscope 1. In this context, the relative spatial position of the marking element 20 should be understood to mean its position and orientation. A deviation between the determined values for the relative spatial position indicates a misalignment between the optical module 2 and the OCT module 3 and can be corrected by a readjustment and, in some cases, also by the use of one or more correction values when processing the data of the microscope image and/or of the OCT image. Since the marking element 20 is arranged on the medical instrument 17, the calibration can be performed when the marking element 20 is in the direct vicinity of the treatment region 16. Consequently, the conditions in the surroundings of the treatment region 16 can be taken into account during the calibration. By way of example, when the microscope 1 is used in ophthalmology, the calibration can be implemented through the lens 15 of the eye 14, and accordingly it is possible to take account of the refractive power of the lens 15 on a patient-individual basis during the calibration. This facilitates a very precise calibration. Moreover, the calibration can be equally performed without problems before, during or following the treatment, and also in treatment pauses. How the calibration is performed in detail will still be explained in more detail below.

Initially, an exemplary embodiment of the form of the marking element 20 is described in detail and how the calibration can be performed is then explained on the basis of this exemplary embodiment.

Figure 2:
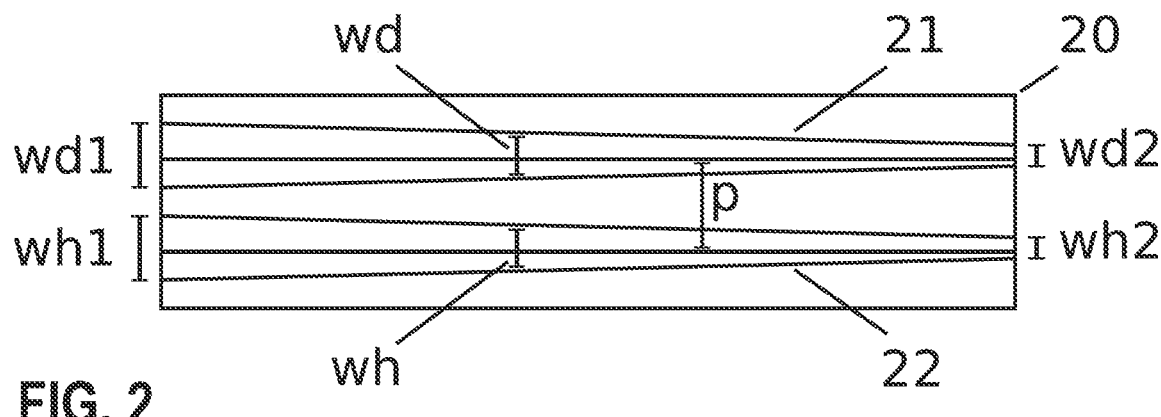
FIG. 2 shows a schematic plan view of the marking element according to an exemplary embodiment of the disclosure.
Figure 3:
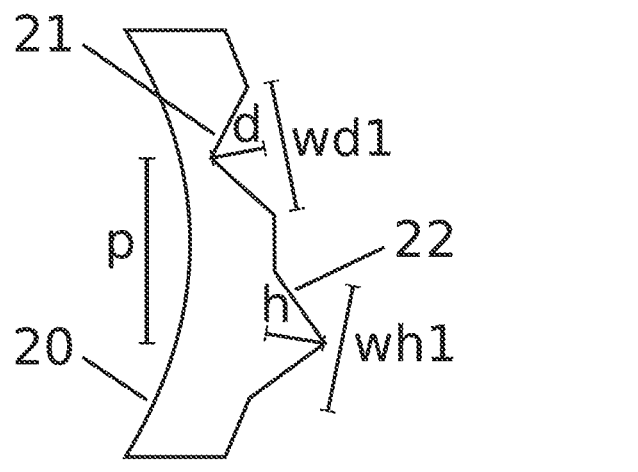
FIG. 3 shows a side view of the marking element shown in FIG. 2 according to an exemplary embodiment of the disclosure.
Figure 4:
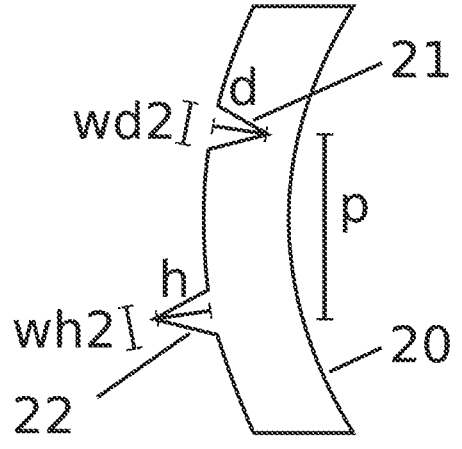
FIG. 4 shows a further side view of the marking element shown in FIG. 2 according to an exemplary embodiment of the disclosure.

FIG. 2 shows a schematic plan view of an exemplary embodiment of the marking element 20 according to an aspect of the disclosure. Associated side views are depicted in FIGS. 3 and 4, with FIG. 3 showing a view of the side depicted to the left in FIG. 2, and FIG. 4 showing a view of the side depicted to the right in FIG. 2, in each case of the marking element 20.

By way of example, the marking element 20 can be in the form of a label which is attached, in particular adhesively bonded, to the shaft 18 of the medical instrument 17. Likewise, the marking element 20 can also be engraved into the shaft 18 of the medical instrument 17, for example with a laser.

In the depicted exemplary embodiment, the marking element 20 is in the form of a cylinder segment of a hollow cylinder and can consequently be easily attached to a cylindrically formed shaft 18. In the depicted exemplary embodiment, the marking element 20 has a significantly greater extent parallel to the axis of the underlying cylinder, that is to say in the horizontal direction of the illustration of FIG. 2, than in the circumferential direction of the underlying cylinder. The extent of the marking element 20 parallel to the axis of the cylinder is also referred to as longitudinal extent below. The extent of the marking element 20 in the circumferential direction of the cylinder is also referred to as transverse extent below. These designations should also apply to exemplary embodiments of the marking element 20 where the extent parallel to the axis of the underlying cylinder is shorter than the extent in the circumferential direction of the underlying cylinder.

The marking element 20 has a depression 21 that runs along its entire longitudinal extent and an elevation 22 that runs along its entire longitudinal extent, that is to say the depression 21 and the elevation 22 each have an elongate form, and each have the same longitudinal extent as the marking element 20. Accordingly, the depression 21 and the elevation 22 are also visible in FIGS. 3 and 4 and, from these figures, it is possible to gather that both the depression 21 and the elevation 22 have a V-shaped cross section in the depicted exemplary embodiment. In the case of the depression 21, the V is oriented such that a concave form arises and, in the case of the elevation 22, the V is oriented such that a convex form arises.

The depression 21 has a constant maximum depth d over its entire longitudinal extent. The maximum depth d is also referred to as depth d below. The elevation 22 has a constant maximum height h over its entire longitudinal extent. The maximum height h is also referred to as height h below. The depth d and the height h have the same value in the depicted exemplary embodiment, that is to say h=d.

Furthermore, the depression 21 has a width wd and the elevation 22 has a width wh. The width wd of the depression 21 is in each case determined where the depression 21 merges into the cylindrical lateral surface of the marking element 20. Analogously, the width wh of the elevation 22 is in each case determined at the foot of the elevation 22, that is to say where the elevation 22 starts to protrude above the cylindrical lateral surface of the marking element 20. Thus, it should be observed that the plan view depicted in FIG. 2 does not show the actual dimensions for the width wd of the depression 21 or for the width wh of the elevation 22 or for the quantities wd1, wd2, wh1, wh2 which are connected therewith and which are still discussed in more detail below, but in each case shows slightly smaller dimensions as a consequence of the projection of these quantities resulting from the plan view. The actual dimensions can be gathered from FIGS. 3 and 4.

The width wd of the depression 21 and the width wh of the elevation 22 each decrease continuously from one end of the longitudinal extent of the marking element 20 to the opposite end. In the region of the end of the longitudinal extent of the marking element 20 that is depicted to the left in FIG. 2, the width wd of the depression 21 is at a maximum and has a value wd1. This region is also depicted in FIG. 3. The width wh of the elevation 22 is also at a maximum there and has a value wh1. In the region of the end of the longitudinal extent of the marking element 20 that is depicted to the left in FIG. 2, the width wd of the depression 21 and the width wh of the elevation 22 are the same, that is to say wd1=wh1.

In the region of the end of the longitudinal extent of the marking element 20 that is depicted to the right in FIG. 2, the width wd of the depression 21 is at a minimum and has a value wd2. This region is also depicted in FIG. 4. The width wh of the elevation 22 is likewise minimal there and has a value wh2 which is identical to the value wd2, that is to say wd2°=°wh2.

The width wd of the depression 21 and the width wh of the elevation 22 each decrease continuously from the end of the longitudinal extent of the marking element 20 depicted to the left in FIG. 2 to the end of the longitudinal extent of the marking element 20 depicted to the right in FIG. 2. In this case, the depression 21 and the elevation 22 in each case have the same width wd°=°wh at the same distance from the end of the longitudinal extent of the marking element 20 depicted to the left in FIG. 2.

The depression 21 and the elevation 22 are arranged at a distance p from one another transversely to the longitudinal extent of the marking element 20. The distance p is defined as the clear distance between the base of the depression 21 and the peak of the elevation 22. In the depicted exemplary embodiment with a depression 21 and an elevation 22 which both have a V-shaped cross section, the distance p moreover corresponds to the distance between the center of the depression 21 and the center of the elevation 22 as measured transversely to the longitudinal extent. This also applies to other exemplary embodiments which have a symmetric form of the depression 21 and the elevation 22 in relation to the longitudinal direction of the marking element 20. The distance p between the depression 21 and the elevation 22 is constant over the entire longitudinal extent of the marking element 20.

The marking element 20 is configured such that it can be detected both by the optical module 2 and by the OCT module 3.

For the detection by way of the optical module 2, the marking element 20 has different levels of reflectivity in the region of the depressions 21 and of the elevations 22. By way of example, the marking element 20 can be configured for specular reflection in the region of the elevations 22 and diffuse scattering in the region of the depressions 21. Consequently, a significant contrast arises between the depressions 21 and the elevations 22 in the microscope images of the marking element 20 that were generated with the aid of the optical module 2.

Since the geometric shape of the marking element 20 and, in particular, the configuration of the depression 21 and of the elevation 22 are known in detail, the relative spatial position of the marking element 20, that is to say its position and orientation, can be determined uniquely from the microscope images on the basis of geometric considerations. The relative position of the medical instrument 17 on which the marking element 20 is arranged can also be uniquely determined in this way.

For the detection by way of the OCT module 3, the marking element 20 is produced from a material that significantly absorbs measurement radiation of the OCT module 3. Unlike the optical module 2, the OCT module 3 does not generate an image representation of the marking element 20, that is to say no plan view of the marking element 20, but instead generates a section through the marking element 20. The relative spatial position of the marking element 20 can likewise be uniquely determined from this section. To this end, it is important for the marking element 20 to have a three-dimensional structure so that an identifiable pattern arises in the sectional representation. This will still be explained in greater detail below.

Figure 5:
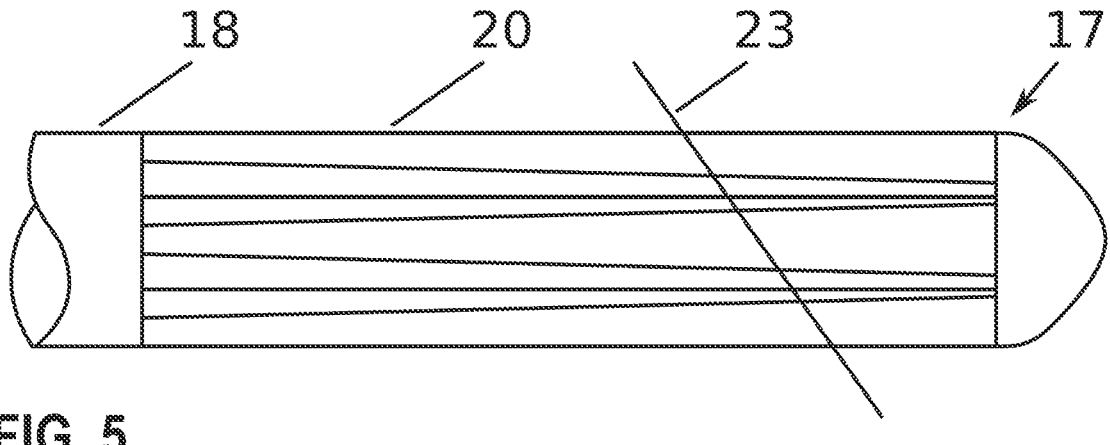
FIG. 5 shows a schematic plan view of the medical instrument having the marking element according to an exemplary embodiment of the disclosure.

FIG. 5 shows a schematic plan view of the medical instrument 17 having the marking element 20 according to an exemplary embodiment of the disclosure.

FIG. 5 plots a line 23 which runs obliquely through the shaft 18 of the medical instrument 17 in the region of the marking element 20. Within the meaning of a cut line, the line 23 specifies the region of the medical instrument 17 that is captured by the B-scan by way of the OCT module 3, that is to say it indicates a scan region. Accordingly, the measuring light of the OCT module 3 is radiated-in within a plane which extends perpendicular to the plane of the drawing in FIG. 5, and which is represented by the line 23.

Figure 6:
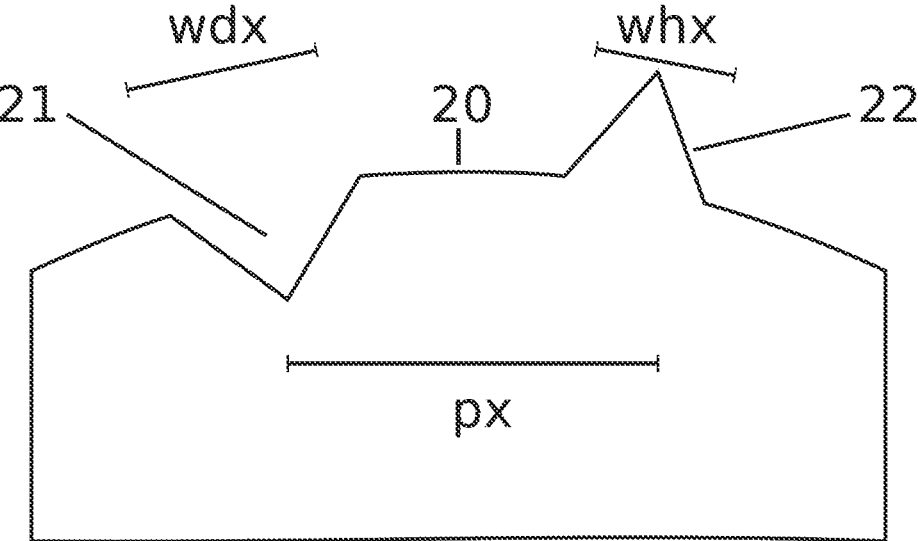
FIG. 6 shows a representation of a B-scan generated by the OCT module.

FIG. 6 shows a representation of a B-scan generated by the OCT module 3. The B-scan was recorded in the geometry depicted in FIG. 5 and corresponds to a section through the medical instrument 17 along the line 23, plotted in FIG. 5, in the region of the marking element 20. The outlines of the depression 21 and of the elevation 22 of the marking element 20 can be clearly identified.

Since the geometry of the marking element 20 is known and the width wd of the depression 21 and the width wh of the elevation 22 change continuously and in a known fashion, in particular linearly, along the longitudinal extent of the marking element 20, the relative spatial position of the marking element 20 can be uniquely determined from the sectional image depicted in FIG. 6. In particular, an angle coordinate for the orientation of the marking element 20 in space can be determined from the distance px between the base of the depression 21 and the peak of the elevation 22 detected in the B-scan since the detected distance px is stretched to a greater or lesser extent relative to the actual distance p depending on the angle coordinate.

A further angle coordinate can be determined from the orientation of the depression 21 and the orientation of the elevation 22.

Moreover, another angle coordinate can be determined from the distortion of the shape of the depression 21 and the distortion of the shape of the elevation 22.

The position coordinates of the marking element 20 can be determined from the width wdx of the depression 21 and the width whx of the elevation 22 detected in the B-scan and from the arrangement of the marking element 20 within the portion illustrated in FIG. 6 or the required displacement for a central arrangement.

To be able to carry out the determination of the relative spatial position of the marking element 20 with a sufficient accuracy in each case, the width wd of the depression 21 and the width wh of the elevation 22 should change as significantly as possible over the longitudinal extent of the marking element 20. The relative spatial position is determined more accurately, the greater the difference between the maximum widths wd1, wh1 and the minimum widths wd2, wh2. In this context, care should be taken that the minimum width wd2 of the depression 21 and the minimum width wh2 of the elevation 22 are not smaller than the lateral resolution of the OCT module 3. The distance p between the depression 21 and the elevation 22 should not be smaller than the lateral resolution of the OCT module 3 either. Analogous statements apply in each case in view of the lateral resolution of the optical module 2. Further, the depth d of the depression 21 and the height h of the elevation 22 should not in each case be smaller than the axial resolution of the OCT module 3.

Since the relative spatial position of the same marking element 20 is in each case determined with the optical module 2 and with the OCT module 3, both types of determination should lead to the same result in each case. A deviation between the results indicates a misalignment of the optical module 2 and of the OCT module 3 relative to one another. Should the deviation assume an inadmissibly high value, a recalibration can be performed on the basis of the results. This can be implemented by changing the alignment of the optical module 2 and of the OCT module 3 relative to one another, which change is completed when the deviation when determining the relative spatial position of the marking element 20 is below an admissible tolerance. Likewise, it is also possible to perform the recalibration with at least one correction value for the further processing of the data output by the optical module 2 and/or by the OCT module 3 to the control device 12.

It is also possible to use the results of the determination of the relative spatial position of the marking element 20 only to determine whether the optical module 2 and the OCT module 3 are still sufficiently calibrated or whether a calibration is needed for the further use of the microscope 1 for a medical examination or a medical treatment. Then, such a calibration can also be performed differently to the procedure described above, in the case of which the calibration is performed on the basis of the relative spatial position of the marking element 20 as determined by the optical module 2 and by the OCT module 3. By way of example, the calibration can be performed in analogous fashion to the calibration within the scope of the production process of the microscope 1.

The described verification of the calibration can be performed, for example, at regular time intervals or every time the system according to the disclosure is activated or for each patient or even multiple times during an examination or continuously or following a prompt by the physician, etc.

Since the marking element 20 is securely arranged on the medical instrument 17, the relative spatial position of the medical instrument 17 can also be determined directly from the relative spatial position of the marking element 20. By way of example, this relationship can be used to determine the relative spatial position of the medical instrument 17 during a medical treatment, for example to facilitate the medical instrument 17 being brought into a desired position with great precision.

Following the calibration, the microscope 1 can be used to assist the medical treatment without this requiring complicated repositioning. Consequently, it is possible to switch without problems and very quickly between a calibration of the microscope 1 and the medical treatment, and so a calibration is even possible during the medical treatment. Should the marking element 20 be in a region detectable both by the optical module 2 and by the OCT module 3 during the medical treatment, the calibration can be allowed to run in the background during the entire medical treatment and the microscope 1 can be continuously recalibrated as a result.

The marking element 20 may also have a different embodiment to the one described above. What is important is that the marking element 20 is detectable both by the optical module 2 and by the OCT module 3 and that it has a geometry that respectively facilitates a unique determination of the relative spatial position of the marking element 20, both with the optical module 2 and with the OCT module 3.

The marking element 20 could also be modified such that it has a first marking region provided for detection by the optical module 2 and a second marking region provided for detection by the OCT module 3. If the relative spatial position of the two marking regions in relation to one another is fixed and known, analogous results can be determined therewith as in the case where a single marking region is used. However, the two marking regions should not be spaced too far apart so that there is no need to reposition the marking element 20 for the purposes of detecting the one marking region by way of the optical module 2 and detecting the other marking region by way of the OCT module 3.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Microscope
2 Optical module

3 OCT module
4 First microscope camera
5 Second microscope camera
6 Frame
7 First illumination device
8 Second illumination device
9 Optical unit
10 OCT detector
11 OCT illumination device
12 Control device
13 Visual display unit
14 Eye
15 Lens
16 Treatment region
17 Medical instrument
18 Shaft
19 Handle
20 Marking element
21 Depression
22 Elevation
23 Line for representing the scan region

What is claimed is:

1. A microscope, comprising:
an optical module;
an optical coherence tomography (OCT) module; and
a control device in communication with the optical module and the OCT module,
wherein the optical module is configured to generate optical image representations,
wherein the OCT module is configured to generate tomographic recordings,
wherein the control device is configured to determine a relative spatial position of a marking element from an optical image representation of the marking element and from a tomographic recording of the marking element, wherein the marking element has an outer shape which is configured such that the relative spatial position of the marking element is determinable from the tomographic recording of the outer shape of the marking element,
wherein the marking element has at least one of a depression and an elevation, wherein
a width of the at least one of the depression and the elevation decreases continuously from an end of a longitudinal extent of the marking element to an opposite end of the longitudinal extent of the marking element, and
where in the marking element is provided on an outer surface of a medical instrument and movable relative to a treatment region.

2. The microscope as claimed in claim 1, wherein the control device is
configured to perform a calibration between the optical module and the OCT module based on
the optical image representation and the tomographic recording of the marking element.

3. A medical instrument, comprising:
a marking element having at least one of a depression and an elevation,
wherein the at least one of the depression and the elevation is embodied such that:
(a) a relative spatial position of the marking element is determinable from an optical image representation of the at least one of the depression and the elevation generated by an
optical module, and

15

(b) the relative position of the marking element is also determinable from a tomographic recording of the at least one of the depression and the elevation generated by an OCT module, wherein the relative spatial position of the marking element defines a position and an orientation of the marking element, wherein the marking element has an outer shape which is configured such that the relative spatial position of the marking element is determinable from the tomographic recording of the outer shape of the marking element, wherein the marking element is provided on an outer surface of the medical instrument and movable relative to a treatment region during a calibration between the optical module and the OCT module, and wherein a width of the at least one of the depression and the elevation decreases continuously from an end of a longitudinal extent of the marking element to an opposite end of the longitudinal extent of the marking element.

4. The medical instrument as claimed in claim 3, wherein the marking element has a locally varying characteristic that is detectable both with the optical module and with the OCT module.

5. The medical instrument as claimed in claim 4, wherein the locally varying characteristic of the marking element has a strictly monotonic form.

6. The medical instrument as claimed in claim 3, wherein the marking element is in a form of a segment of a hollow cylinder.

7. A system, comprising:

a microscope;

a marking element; and a control device, wherein:

the marking element has at least one of a depression and an elevation, a width of the at least one of the depression and the elevation decreases continuously from an end of a longitudinal extent of the marking element to an opposite end of the longitudinal extent of the marking element, the marking element is provided on an outer surface of a medical instrument and movable relative to a treatment region, the microscope has an optical module, with which an optical image representation of the marking element is generable, the microscope has an OCT module, with which a tomographic recording of the marking element is generable, the marking element is configured such that the relative spatial position of the marking element is determinable both from the optical image representation of the marking element and from the tomographic recording of the marking element, the control device is configured to determine the relative spatial position of the marking element both from the optical image representation of the marking element and from the tomographic recording of the marking element, and the marking element has an outer shape which is configured such that the relative spatial position of the marking element is determinable from the tomographic recording of the outer shape of the marking element.

8. The system as claimed in claim 7, wherein the marking element has a locally varying characteristic that is detectable both with the optical module and with the OCT module.

9. The system as claimed in claim 8, wherein the locally varying characteristic of the marking element has a strictly monotonic form.

10. The system as claimed in claim 7, wherein the marking element is in a form of a segment of a hollow cylinder.

11. The system as claimed in claim 7, further comprising a medical instrument, wherein the marking element is arranged on the medical instrument.

12. A method for calibrating a microscope, the microscope having an optical module and an OCT module, the method comprising:

generating an optical image representation of a marking element with the optical module;

generating a tomographic recording of the marking element with the OCT module;

carrying out a first determination of the relative spatial position of the marking element, which leads to a first result, based on the optical image representation of the marking element; and carrying out a second determination of the relative spatial position of the marking element, which leads to a second result, based on the tomographic recording of the marking element, wherein the marking element has an outer shape which is configured such that the relative spatial position of the marking element is determinable from the tomographic recording of the outer shape of the marking element, wherein the marking element has at least one of a depression and an elevation, wherein a width of the at least one of the depression and the elevation decreases continuously from an end of a longitudinal extent of the marking element to an opposite end of the longitudinal extent of the marking element, and wherein the marking element is provided on an outer surface of a medical instrument and movable relative to a treatment region.

13. The method as claimed in claim 12, further comprising:

determining a deviation between the first result and the second result.

14. The method as claimed in claim 13, further comprising:

determining whether an inadmissibly significant misalignment is present between the optical module and the OCT module based on the determined deviation.

15. A non-transitory computer-readable storage medium with a computer program including a program code that when executed by a processor causes the processor to at least one of:

carry out the method as claimed in claim 13, and control the implementation of said method.

16. The method as claimed in claim 12, further comprising:

triggering the calibration when a specified condition is present.

17. The method as claimed in claim 12, wherein the calibration is performed during a medical treatment.

* * * * *